United States Patent [19]

Genese et al.

[11] 4,417,577

[45] * Nov. 29, 1983

[54] GRAVITATIONAL FLOW SYSTEM FOR THE SEQUENTIAL ADMINISTRATION OF MEDICAL LIQUIDS

[75] Inventors: Joseph N. Genese, Waukegan; Andrew J. Muetterties, Mundelein, both of Ill.

[73] Assignee: Abbott Laboratories, North Chicago, Ill.

[*] Notice: The portion of the term of this patent subsequent to Feb. 28, 1997 has been disclaimed.

[21] Appl. No.: 223,642

[22] Filed: Jan. 9, 1981

Related U.S. Application Data

[63] Continuation-in-part of Ser. No. 167,948, Jul. 14, 1980, Pat. No. 4,316,460, which is a continuation-in-part of Ser. No. 16,461, Feb. 28, 1979, Pat. No. 4,256,104.

[51] Int. Cl.³ .............................................. A61M 5/00
[52] U.S. Cl. ..................................... 604/81; 137/113; 222/145; 604/126; 604/31
[58] Field of Search ............ 128/214 R, 214 G, 214.2, 128/227; 137/112–114, 173, 198, 199; 222/145

[56] References Cited

U.S. PATENT DOCUMENTS

| | | | |
|---|---|---|---|
| 4,237,880 | 12/1980 | Genese | 128/214 G |
| 4,250,879 | 2/1981 | Muetterties | 128/214 G |
| 4,316,460 | 2/1982 | Genese et al. | 128/214 R |

Primary Examiner—Dalton L. Truluck
Attorney, Agent, or Firm—Robert S. Beiser; Robert L. Niblack

[57] ABSTRACT

A gravitational flow system for the sequential administration of medical liquids to a patient comprises a primary container connected to a primary tube, a secondary container connected to a secondary tube, and a combined air barrier and liquid sequencing valve which connects them and is in fluid communication with a common tube extending to the patient. A primary flow control device is positioned in the primary flow path and a secondary flow control device is positioned in the secondary flow path. In operation, the system dispenses primary liquid unless interrupted by a flow of secondary liquid. In that instance, primary liquid flow is cut off by an air capturing pocket. At the same time, a plurality of air barriers prevent infusion of air into the patient.

9 Claims, 4 Drawing Figures

GRAVITATIONAL FLOW SYSTEM FOR THE SEQUENTIAL ADMINISTRATION OF MEDICAL LIQUIDS

This application is a continuation-in-part of U.S. Ser. No. 167,948, filed July 14, 1980, now U.S. Pat. No. 4,316,460 which is a continuation-in-part of U.S. Ser. No. 16,461, now U.S. Pat. No. 4,256,104 filed Feb. 28, 1979, both of which are hereby incorporated by reference.

BACKGROUND OF THE INVENTION

The present invention relates to systems and equipment sets for the administration of medical liquids to a patient, and more particularly, to systems and equipment sets for the sequential administration of a plurality of medical liquids employing a novel air capturing pocket in the flow path of one liquid to prevent the passage of liquid through that path when a second liquid is being dispensed.

The parenteral administration of medical liquids to patients is a long established practice. Liquids including amino acids, dextrose, electrolytes, and saline are commonly administered to patients over prolonged periods of time. Generally, these liquids are administered from a glass bottle or plastic bag suspended above the patient and containing 250-1,000 ml. of the liquid. Such prolonged infusions commonly are administered at a flow rate of 10-150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at flow rate of 50-250 ml./hr.

Abbott Laboratories, North Chicago, Ill. manufactures a Y-type set for the sequential administration of primary and secondary liquids. These VENOSET® piggyback sets allow the prolonged infusion of a primary liquid to be temporarily halted by means of a backcheck valve in the primary flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corporation, and entitled "Medical Administration Set for Dispensing Plural Medical Liquids." Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion."

An inherent disadvantage of the above-mentioned prior art medical liquid administration systems is that they each resume the flow of primary liquid at the rate the secondary liquid had been flowing. Because the preferred rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the Y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

In order to solve this problem, various filter systems for preventing air passing into a patient may be found in U.S. Pat. Nos. 3,854,907 (Rising), 3,149,758 (Bush), and 4,116,646 (Edwards), all assigned to Millipore Corporation. All of these devices utilize a hydrophilic membrane filter. However, the use of an air barrier to allow automatic sequencing of primary and secondary medical liquids and the further use of preset primary and secondary flow controls was first disclosed in U.S. Ser. No. 16,461 filed Feb. 28, 1979, of which this application is a continuation-in-part.

From the foregoing, it will be apparent that improved systems for the sequential administration of medical liquids at dual flow rates would be highly advantageous to the medical profession.

SUMMARY OF THE INVENTION

Accordingly, the primary advantage of the present invention over the prior art is to provide an equipment set for the sequential administration of medical liquids at preset dual flow rates that will not draw air from the secondary container when the secondary liquid has been depleted.

In accordance with this and other advantages, there is provided by the present invention, as disclosed in Ser. No. 167,948, a gravitational flow system comprising a primary container in fluid communication with a primary tube, a secondary container at a height greater than that of the primary container, in fluid communication with a secondary tube, and an air barrier and liquid sequencing valve connected to the primary and secondary tubes with a common tube extending to the patient. A primary flow control is positioned in the primary flow path for adjusting the rate of flow of primary liquid through the primary liquid flow path at a rate independent of the secondary liquid. Similarly, a secondary flow control is positioned in the secondary liquid flow path for adjusting the flow rate of the secondary liquid therethrough. The combined air barrier and liquid sequencing valve allows primary liquid to flow whenever the height of the primary liquid is greater than or equal to the height of the secondary liquid, but prevents primary liquid from flowing when the primary container is at a height less than the height of the secondary container in the system.

The combined air barrier and liquid sequencing valve of the present invention comprises a housing divided into first, second and third chambers by a plurality of partitions. One of the partitions is disposed horizontally within the housing so as to divide the housing into first and second chambers and to seal the first chamber from the second chamber. The first chamber has an inlet port to allow the passage of primary fluid into the first chamber, and an outlet port, preferably incorporated in the bottom of the first chamber to allow primary liquid to pass from the first chamber into the second chamber. The outlet port is also covered by a hydrophilic membrane which prevents air from moving between the first chamber and the second chamber when the hydrophilic membrane is moistened. An inlet port to the second chamber admits secondary liquid and a plurality of outlet ports from the second chamber allow both primary and secondary liquid to pass therethrough.

One of the essential features of the invention, first disclosed in Ser. No. 167,948, is an air capturing pocket below the previously mentioned hydrophilic membrane in the outlet port from the first chamber to the second chamber. The air capturing pocket receives residual air within the second chamber when secondary liquid is being dispensed. Because the pressure of the secondary liquid is greater then that of the primary liquid, the partial pressure of the air below the hydrophilic membrane is greater than the pressure of the primary liquid seeking to pass therethrough. As a result, the flow of primary liquid is interrupted for so long as the pressure of the secondary liquid is greater then that of the primary liquid; i.e., until the secondary liquid is substantially depleted.

In a preferred embodiment, the air capturing pocket is bordered on one side by a third chamber which extends downwardly below the horizontal partition. The third chamber also has an inlet port incorporated at its base and sealed by a hydrophilic membrane, so that air can be entrapped below the outlet between the first and second chambers during dispensing the primary liquid. An outlet port above the inlet port of the third chamber extends through the housing so that secondary liquid may pass upwardly through the inlet port, through the third chamber and out of the outlet port during dispensing of secondary light.

As an additional feature of the invention, a flexible diaphragm may be disposed across and seal a portion of the previously mentioned horizontal partition. The flexible diaphragm is constructed and positioned so as to be distorted or stretched by the pressure of the primary liquid toward the second chamber during dispensing of primary liquid. This displaces air within the second chamber towards the area below the inlet to the third chamber, which in turn prevents primary liquid from flowing through the inlet to the third chamber. When secondary liquid is being dispensed, the diaphragm is distorted or stretched toward the first chamber. Air is thereby displaced from below the inlet to the third chamber towards the air capturing pocket, thus permitting the flow of secondary liquid through the inlet to the third chamber, and preventing the flow of primary liquid through the outlet from the first chamber.

In a preferred embodiment, the inlet to the first chamber is positioned near the top of the housing and the inlet port to the second chamber is positioned on the side of the housing. The outlet port for primary liquid from the second chamber is positioned proximate the bottom of the second chamber. The second chamber also includes an inlet to the third chamber which is positioned proximate the middle of the housing. The third chamber is preferably formed as an integral portion of the first chamber. Similarly, the horizontal partition is preferably formed as an integral portion of the housing. The first chamber also may include a closable air vent sealed by a hydrophobic membrane which allows air to escape from the housing during administration of primary liquid.

The previously mentioned flexible diaphragm preferably comprises an elastomeric sheet sealed across and opening in the horizontal partition. The elastomeric sheet has sufficient flexibility to deform under the relatively low pressure exerted by a conventional container of medical liquid; i.e., 50 to 1000 ml. of solution. At the same time, the flexible sheet is sufficiently resilient to return to a substantially plainer configuration in the absence of such pressure.

The previously mentioned gravitational flow system utilizes the combined air barrier and liquid sequencing valve described above. The primary and secondary tubes are connected to the combined air barrier and liquid sequencing valve as previously described; i.e., primary tube enters the housing at the top thereof and the secondary tube enters the housing at the side thereof. The primary tube continues from the housing and the secondary tube continues from the opposite side of the housing. The distal ends of the primary and secondary tubes meet in a common tube which extends to the patient. As a result, when in operation, primary and secondary liquids may be administered independently at preset rates without danger of the passage of air into the vein of the patient.

As an additional safety feature, one or more hydrophilic filters may be interposed in the primary, secondary or common flow paths below the combined air barrier and liquid sequencing valve in order to further insure the prevention of inadvertent administration of air to the patient.

DETAILED DESCRIPTION OF THE PREFERRED EMBODIMENT

Figure 1:
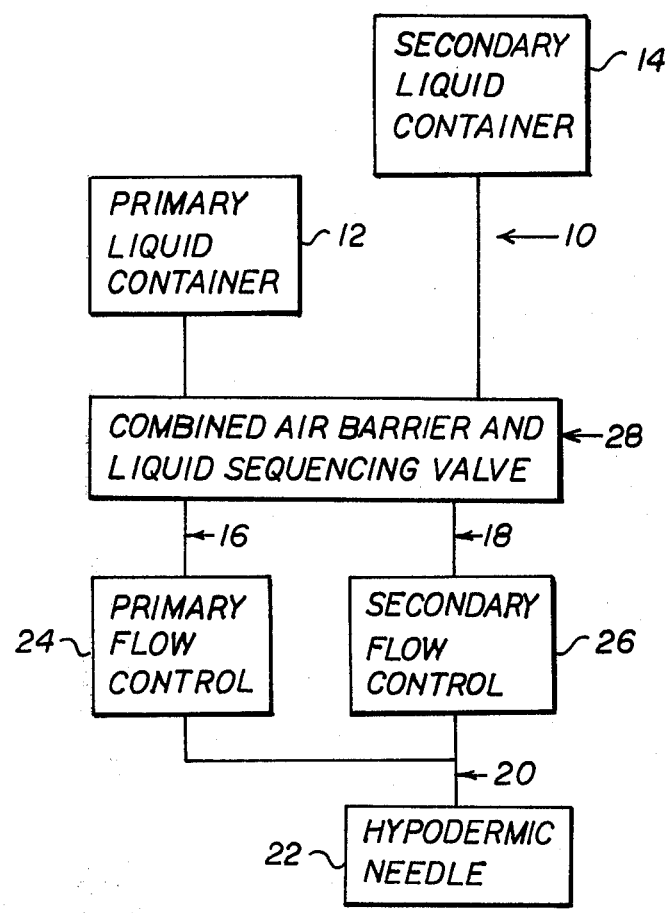
FIG. 1 of the drawings is a schematic diagram of a gravitational flow system for the sequential administration of medical liquids.

While this invention is susceptible to embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

As seen in FIG. 1 of the drawings, improved gravitational flow system 10 comprises a primary liquid container 12, a secondary liquid container 14, a primary tube 16 in fluid communication with primary liquid container 12, a secondary tube 18 in fluid communication with secondary liquid container 14, a common liquid tube 20 in fluid communication with both primary liquid tube 16 and secondary liquid tube 18, and a hypodermic needle 22 at the proximal end of common tube 20. Interposed on primary tube 16 is primary flow control 24 which regulates the rate of flow of the primary liquid. Similarly interposed on secondary tube 18 is secondary flow control 26 which controls the flow of secondary liquid. Interposed in communication with both primary tube 16 and secondary tube 18 are a combined air barrier and liquid sequencing valve 28 which permits the flow of primary liquid when the primary liquid container 12 is at a height equal to or greater than the secondary liquid container 14. However, when secondary liquid container 14 is at a height greater than primary liquid container 12, combined air barrier and liquid sequencing valve 28 prevents the flow of primary liquid and allows the flow of secondary liquid.

Figure 2:
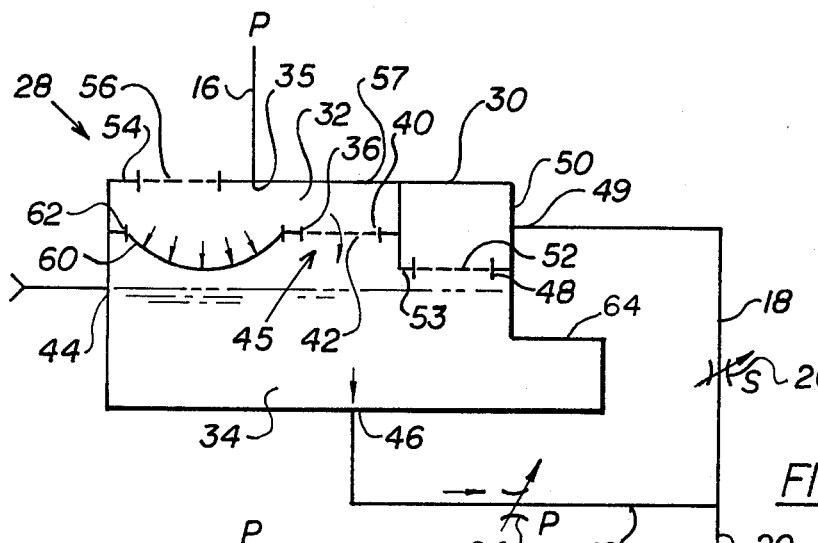
FIG. 2 of the drawings is a vertical section of the combined air barrier and liquid sequencing valve of FIG. 1 and showing flow of primary liquid.

Combined air barrier and liquid sequencing valve 28 as seen in FIG. 2 comprises a housing 30 divided into first chamber 32 and second chamber 34 by a substantially horizontal partition 36. Primary liquid from primary tube 16 enters first chamber 32 through port 35. Partition 36 has an outlet port 40 incorporated therein for the passage of primary liquid from first chamber 32 to second chamber 34. Included in outlet port 40 is a hydrophilic membrane 42 which covers outlet port 40 and prevents air from moving between first chamber 32 and second chamber 34, once membrane 42 has been wetted. Second chamber 34 includes an inlet port 44 for the admission of secondary liquid and a number of outlet ports such as port 46 for the passage of primary and secondary liquid, and port 48 for the passage of secondary liquid therefrom. When secondary liquid passes through inlet port 44 into second chamber 34, residual air is trapped in the area below outlet port 40 and hydrophilic membrane 42, known as air pocket 45. The presence of this residual air in air pocket 45 prevents the passage of primary liquid from first chamber 32 into second chamber 34, because the partial pressure in second chamber 34 is greater than the pressure in first chamber 32 due to the greater pressure of the secondary liquid then the primary liquid. As a result, the flow of primary liquid is halted.

Figure 3:
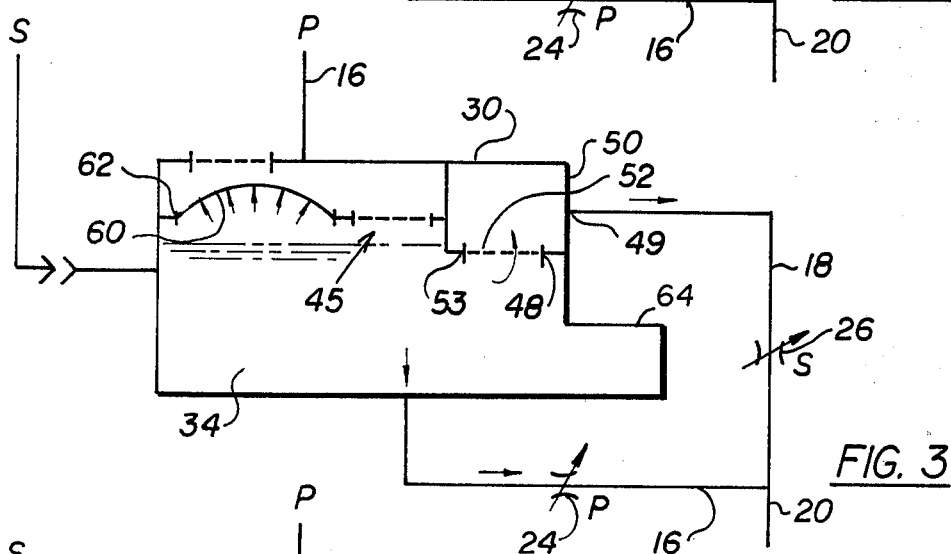
FIG. 3 of the drawings is a vertical section of the combined air barrier and liquid sequencing valve of FIG. 2 showing in particular the administration of the secondary liquid through the valve.

As shown in FIG. 3, housing 30 also includes a third chamber 50 incorporated therein. A hydrophilic membrane 52 is disposed across and seals port 48 which is disposed in the base 53 of third chamber 50. When secondary liquid passes into second chamber 34, it is under sufficient pressure to displace the air below port 48 into air capturing pocket 45. Secondary liquid is then able to enter and pass through third chamber 50 and out of port 49, located on the side of housing 30.

As further shown in FIG. 3, third chamber 50 is integrally formed as part of second chamber 34. Second chamber 34, first chamber 32 and housing 30 may be constructed of conventional intravenous valve materials such as plastic. Housing 30 may also include an air vent 54 positioned proximate the top of housing 30. Covering air vent 54 is a hydrophobic membrane 56, which permits air to be vented therethrough, but which prevents primary liquid from escaping housing 30.

As best illustrated in FIG. 2, in a preferred embodiment, disposed across horizontal partition 36 is a flexible diaphragm 60, preferably constructed of a silicone elastomer material. Diaphragm 60 seals opening 62 through horizontal partition 36. Flexible diaphragm 60 is constructed to be distended or stretched downward toward second chamber 34 during dispensing of primary liquid into first chamber 32. As a result, the space in second chamber 34 for residual air is reduced. Air is thereby forced into the space below hydrophilic membrane 52 leading into third chamber 50. The flow of any residual primary liquid into third chamber 50 is thereby prevented. It should be noted that while housing 30 is divided into first and second chambers by horizontal partition 36, as in FIG. 2, the present invention encompasses the use of any number of partitions, either vertical or horizontal, which employ the greater pressure of the secondary liquid within an air capturing pocket, to cut off the flow of primary liquid.

Figure 4:
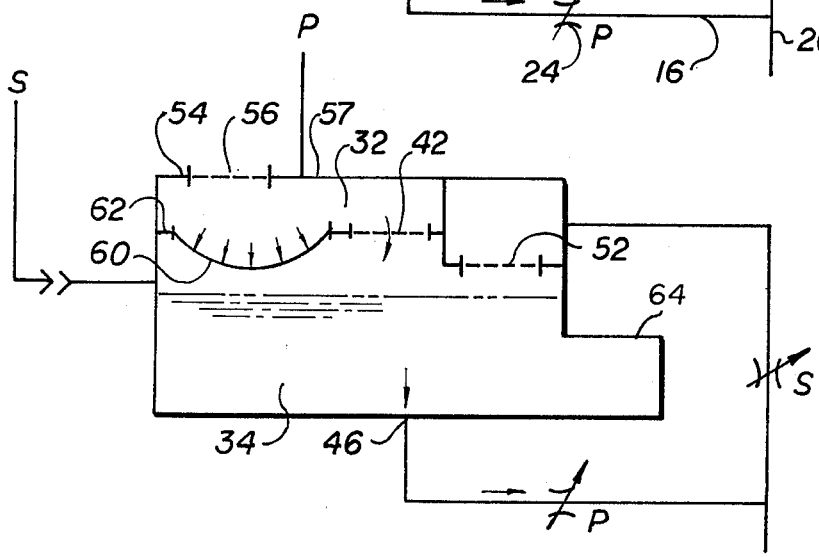
FIG. 4 of the drawings is a vertical section of the combined air barrier and liquid sequencing valve of FIG. 2 showing the resumption of flow of primary liquid.

As best seen in FIG. 3, when secondary liquid is admitted into second chamber 34 through port 44, flexible diaphragm 60 is displaced upwardly into first chamber 32, thereby increasing the space available in air capturing pocket 45. The air below hydrophilic membrane 52 is then able to pass upwardly into air capturing pocket 45 and into the curved bubble created by flexible diaphragm 60. Secondary liquid is thereby able to pass through hydrophilic membrane 52 into third chamber 50 and out of port 49. When secondary liquid is depleted, the pressure is reduced and flexible diaphragm 60 returns to a substantially planar configuration. As best seen in FIG. 4, primary liquid is then allowed to flow through hydrophilic membrane 42 so that primary liquid again forces flexible diaphragm 60 downwardly into second chamber 34.

OPERATION OF THE SYSTEM

In operation, as illustrated in FIG. 2, system 10 may be primed by allowing primary liquid to pass from primary liquid container 12 into combined air barrier and liquid sequencing valve 28. Primary flow control 24 is in the closed position. Valve 28 is inverted so that chamber 64 is in the raised position; positioned above the remainder of valve 28 and primary liquid enters housing 30 through port 35 and passes into first chamber 32. The primary liquid then passes through port 40 and hydrophilic membrane 42 into second chamber 34. The primary liquid then passes downward in second chamber 34 and out port 46. A desired quantity of air is trapped in chamber 64. Membrane 52 is also wetted in this position. Valve 28 may then be returned to a horizontal position and primary flow control 24 set at a desired rate.

As shown in FIG. 3, when secondary liquid enters second chamber 34 through port 44, the higher pressure of the secondary liquid causes air to be displaced from under port 48 into air pocket 45. This allows passage of secondary liquid into third chamber 50 and out of port 49. The air in air capturing pocket 45 is consequently under greater pressure than the primary liquid, due to the force of the secondary liquid upon it. Primary liquid is thereby prevented from flowing through hydrophilic membrane 42 into second chamber 34. Thus, secondary liquid will flow from second chamber 34 through ports 46 and 48 as long as the pressure of the secondary liquid is greater than that of the primary liquid. When the pressure of the secondary liquid becomes less than that of the primary liquid, (FIG. 4), primary liquid will again flow through hydrophilic membrane 42 into second chamber 34. Primary liquid will then begin to flow out of port 46.

The foregoing description and drawings merely explain and illustrate the invention and the invention is not limited thereto except insofar as the appended claims are so limited and those skilled in the art who have the disclosure before them will be able to make modifications and variations therein without departing from the scope of the invention.

We claim:

1. A combined air barrier and liquid sequencing valve for the sequential administration of a primary liquid and a secondary liquid comprising:
   a housing divided into three or more chambers by a plurality of partition members;
   one of said partition members being disposed substantially horizontally within said housing so as to divide said housing into first and second chambers and to seal said first chamber from said second chamber;
   said first chamber in said housing having an inlet port incorporated therein for the passage of primary liquid into said first chamber, and an outlet port incorporated therein for the passage of said primary liquid from said first chamber into the second chamber, said outlet port from said first chamber including a hydrophilic membrane incorporated therein and covered thereby for the prevention of air movement between said first chamber and said second chamber when said hydrophilic membrane is moistened;
   an inlet port to said second chamber for the admission of secondary liquid and a plurality of outlet ports from said second chamber for the passage of primary and secondary liquid; and
   an air capturing pocket proximate said hydrophilic membrane covering said outlet port from said first chamber to said second chamber, said air capturing pocket being constructed and arranged for the reception of residual air within said second chamber proixmate said hydrophilic membrane when said secondary liquid is dispensed into said second chamber whereby the flow of said primary liquid is interrupted for so long as the pressure of said secondary liquid is greater than that of said primary liquid;
   said air capturing pocket being defined as the area below said outlet port from said first chamber to said second chamber, enclosed on one side by a third chamber extending at least partially downward below said horizontal partition, said third chamber having an inlet port from said second chamber incorporated at its base and sealed by a hydrophilic membrane whereby air may be entrapped below said outlet between said first and second chambers during dispensing of said primary liquid, said third chamber further having an outlet port positioned above said inlet port and opening out of said housing whereby secondary liquid may pass upwardly through said inlet port into said third chamber and out of said outlet port during dispensing of said secondary liquid.

2. The combined air barrier and liquid sequencing valve as defined in claim 1 and further comprising:
   a flexible diaphragm member disposed across and sealing a portion of said horizontal partition, said flexible diaphragm member being constructed and arranged for distention towards said second chamber during dispensing of said primary liquid, so as to displace air within said second chamber towards the area below said inlet to said third chamber, thereby preventing the flow of liquid therethrough, and being constructed and arranged for distention towards said first chamber during dispensing of said secondary liquid whereby said air is displaced from below said third chamber inlet towards said air capturing pocket, thereby permitting the flow of secondary liquid through said inlet, into said third chamber, through said third chamber and out of said housing.

3. The system defined in claim 1, wherein said inlet port to said first chamber is positioned proximate the top thereof for the admission of primary liquid and said inlet port to said second chamber is positioned proximate the side thereof for the admission of secondary liquid and the interruption of said flow of primary liquid, and at least one of said outlet ports from said second chamber is positioned proximate the bottom thereof for the selective dispensing of primary or secondary liquid.

4. The system as defined in claim 3 wherein said inlet port to said third chamber is positioned proximate the middle of said housing for the vertical flow of secondary liquid therethrough.

5. The system defined in claim 1, wherein said third chamber is integrally formed as a portion of said first chamber.

6. The system defined in claim 1 or 2, wherein said first chamber further includes a closable air vent.

7. The system defined in claim 6, wherein said air vent is covered by a hydrophobic membrane.

8. The combined air barrier and liquid sequencing valve as defined in claim 2, wherein said flexible diaphragm member comprises an elastomeric sheet sealed across an opening in said horizontal partition and having sufficient flexibility to deform under the relatively low pressure exerted by a conventional container of medical liquid of from 50 to 1000 ml. of solution, and sufficient resiliency to return to a substantially planar configuration in the absence of said pressure.

9. The gravitational flow system as defined in claim 7, and further comprising one or more hydrophilic filters interposed in said primary, secondary or common flow paths below said combined air barrier and liquid sequencing valve for the prevention of inadvertent administration of air to a patient.

* * * * *